(12) United States Patent
Hall

(10) Patent No.: US 7,891,232 B2
(45) Date of Patent: Feb. 22, 2011

(54) RIGID PARTICULATE MATTER SENSOR

(75) Inventor: Matthew Hall, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 219 days.

(21) Appl. No.: 12/275,791

(22) Filed: Nov. 21, 2008

(65) Prior Publication Data

US 2010/0126248 A1    May 27, 2010

(51) Int. Cl.
*G01N 37/00*    (2006.01)
(52) U.S. Cl. ..................... 73/28.01
(58) Field of Classification Search ............... 73/28.01, 73/28.02
See application file for complete search history.

(56) References Cited

U.S. PATENT DOCUMENTS

| | | | |
|---|---|---|---|
| 2,307,602 A | 1/1943 | Penney | |
| 3,826,574 A | 7/1974 | Brown, Jr. | |
| 4,121,458 A | 10/1978 | Fort | |
| 4,656,832 A | 4/1987 | Yukihisa et al. | |
| 4,713,964 A | 12/1987 | Ioannides | |
| 4,939,466 A | 7/1990 | Johnson et al. | |
| 5,008,628 A | 4/1991 | Kirgmont et al. | |
| 5,104,513 A | 4/1992 | Lee et al. | |
| 5,264,272 A | 11/1993 | Tanabe et al. | |
| 5,290,606 A | 3/1994 | Hestevik et al. | |
| 5,302,935 A | 4/1994 | Chatterjee | |
| 5,608,155 A | 3/1997 | Ye et al. | |
| 5,795,454 A | 8/1998 | Friese et al. | |
| 5,892,140 A | 4/1999 | Wood | |
| 5,922,946 A | 7/1999 | Hirota et al. | |
| 5,942,190 A | 8/1999 | Kato et al. | |
| 6,076,393 A | 6/2000 | Kato et al. | |
| 6,161,421 A | 12/2000 | Fang et al. | |
| 6,214,208 B1 | 4/2001 | Ando et al. | |
| 6,557,393 B1 | 5/2003 | Gokhfeld et al. | |

(Continued)

FOREIGN PATENT DOCUMENTS

DE    4236711    5/1993

(Continued)

OTHER PUBLICATIONS

Young, Lee W., "International Search Report", (Aug. 15, 2008),1-3.

(Continued)

*Primary Examiner*—Hezron Williams
*Assistant Examiner*—Tamiko D Bellamy
(74) *Attorney, Agent, or Firm*—Jeffrey T. Holman

(57) ABSTRACT

A sensor to detect particulate matter. The sensor includes a first rigid tube, a second rigid tube, a detection surface electrode, and a bias surface electrode. The second rigid tube is mounted substantially parallel to the first rigid tube. The detection surface electrode is disposed on an outer surface of the first rigid tube. The detection surface electrode is disposed to face the second rigid tube. The bias surface electrode is disposed on an outer surface of the second rigid tube. The bias surface electrode is disposed to face the detection surface electrode on the first rigid tube. An air gap exists between the detection surface electrode and the bias surface electrode to allow particulate matter within an exhaust stream to flow between the detection and bias surface electrodes.

33 Claims, 5 Drawing Sheets

U.S. PATENT DOCUMENTS

| | | |
|---|---|---|
| 6,634,210 B1 | 10/2003 | Bosch et al. |
| 6,705,152 B2 | 3/2004 | Routkevitch et al. |
| 6,763,699 B1 | 7/2004 | Hunter et al. |
| 6,971,258 B2 | 12/2005 | Rhodes et al. |
| 7,041,153 B2 | 5/2006 | Totoki et al. |
| 7,063,731 B2 | 6/2006 | Roe |
| 7,406,855 B2 | 8/2008 | Tikkanen et al. |
| 7,714,299 B2 * | 5/2010 | Wang et al. ............... 250/397 |
| 2003/0014966 A1 | 1/2003 | Hirota et al. |
| 2003/0121251 A1 | 7/2003 | Kelley et al. |
| 2005/0178675 A1 | 8/2005 | Hall |
| 2006/0016246 A1 | 1/2006 | Rhodes et al. |
| 2007/0089399 A1 | 4/2007 | Rhodes et al. |
| 2007/0271903 A1 | 11/2007 | Rhodes et al. |
| 2008/0265870 A1 | 10/2008 | Nair et al. |
| 2009/0056416 A1 | 3/2009 | Nair et al. |

FOREIGN PATENT DOCUMENTS

| | | |
|---|---|---|
| DE | 19536705 | 3/1997 |
| DE | 19817402 | 9/1999 |
| JP | 60-123757 | 7/1985 |
| JP | 64-20441 | 1/1989 |

OTHER PUBLICATIONS

Young, Lee W., "Written Opinion of the International Searching Authority", (Aug. 15, 2008),1-10.

Young, Lee W., "International Search Report", (Nov. 25, 2008),1-2.

Young, Lee W., "Written Opinion of the International Searching Authority", (Nov. 25, 2008),1-6.

Hauser, "Method for Measuring Particles in Gas Flow e.g. vehicle exhaust", DE19536705, (Apr. 3, 1997),Abstract.

Hauser, "Sensor Device for Quantitative Evaluation of Particles Suspended in Gas Flow, e.g. smoke particles in diesel engine exhaust gas", DE19817402, (Sep. 30, 1999),Abstract.

Moosmueller, et al., "Time Resolved Characterization of Diesel Particulate Emissions", *Environmental Science and Technology*, vol. 35, No. 4, (2001),781-787.

Olsen, Kaj K., "International Search Report", (Feb. 13, 2004),1-5.

McCall, Eric S., "Office-Action for U.S. Appl. No. 11/039,365 sent Feb. 2, 2009", 1-6.

Hauser, "English Translation of DE-19536705", (Apr. 3, 1997),1-8.

Hauser, "English Translation of DE-19817402", (Sep. 30, 1999),1-6.

* cited by examiner

RIGID PARTICULATE MATTER SENSOR

U.S. GOVERNMENT INTEREST

This invention was made with government support under Contract No. DE-FC26-06NT42966 awarded by the U.S. Department of Energy. The government has certain rights in the invention.

BACKGROUND

Internal combustion engines (e.g., diesel engines) typically generate an exhaust flow that contains varying amounts of particulate matter (PM). The amount and size distribution of particulate matter in the exhaust flow tends to vary with engine operating conditions, such as fuel injection timing, injection volume, injection pressure, or the engine speed to load relationship. Adjustment of these conditions may be useful in reducing particulate matter emissions and average particle size of the particulate matter from the engine. Reducing particulate matter emissions from internal combustion engines is environmentally favorable. In addition, particulate matter measurements for diesel exhaust is useful for on-board (e.g., mounted on a vehicle) diagnostics of PM filters and reduction of emissions through combustion control.

Conventional technologies that may be used for on-board monitoring of particulate matter in exhaust flow include the use of wire electrodes in sensor applications. Wire electrode sensors apply a high voltage between two electrodes and measure the current or charge between the electrodes. The electrode measurement is correlated with a specific particulate matter concentration. However, wire electrode sensors are subject to the de-calibration and baseline drift of the sensor due to accumulation of soot (i.e., particulate matter deposit) on and between the electrodes. Wire electrodes are also subject to vibration, which changes the distance between the electrodes. As the distance between the electrodes changes according to the vibration of the electrodes, the varying distance introduces error in the particulate matter reading.

SUMMARY

Embodiments of a sensor are described. In one embodiment, the sensor includes a first rigid tube, a second rigid tube, a detection surface electrode, and a bias surface electrode. The second rigid tube is mounted substantially parallel to the first rigid tube. The detection surface electrode is disposed on an outer surface of the first rigid tube. The detection surface electrode is disposed to face the second rigid tube. The bias surface electrode is disposed on an outer surface of the second rigid tube. The bias surface electrode is disposed to face the detection surface electrode on the first rigid tube with a gap between the detection surface electrode and the bias surface electrode. Other embodiments of the sensor are also described.

Embodiments of a system are also described. In one embodiment, the system is a system for detecting particulate matter. The system includes a sensor and an electronic controller. The sensor is configured to detect the particulate matter within an exhaust stream. The sensor includes a pair of non-conductive rigid tubes, a detection surface electrode, and a bias surface electrode. The detection surface electrode is disposed on one of the rigid tubes and faces the other non-conductive rigid tube. The bias surface electrode is disposed on the other rigid tube. The bias surface electrode faces the detection surface electrode and is separated from the detection surface electrode by an air gap for passage of a portion of the exhaust stream through the air gap. The electronic controller is configured to determine an amount of the particulate matter within the exhaust stream. Other embodiments of the system are also described.

Embodiments of a method are also described. In one embodiment, the method is a method for making a particulate matter sensor. The method includes disposing a detection surface electrode on an outer surface of a first non-conductive rigid tube. The method also includes disposing a bias surface electrode on an outer surface of a second non-conductive rigid tube. The bias and detection surface electrodes face each other and are separated by an air gap for passage of a portion of an exhaust stream through the air gap. The method also includes disposing a first heater on a first heater post within an internal cavity of the first rigid tube. The first heater applies heat to burn off particulate matter from the first non-conductive rigid tube. The method also includes disposing a second heater on a second heater post within an internal cavity of the second rigid tube. The second heater applies heat to burn off particulate matter from the second non-conductive rigid tube. Other embodiments of the method are also described.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

Throughout the description, similar reference numbers may be used to identify similar elements.

DETAILED DESCRIPTION

Figure 1:
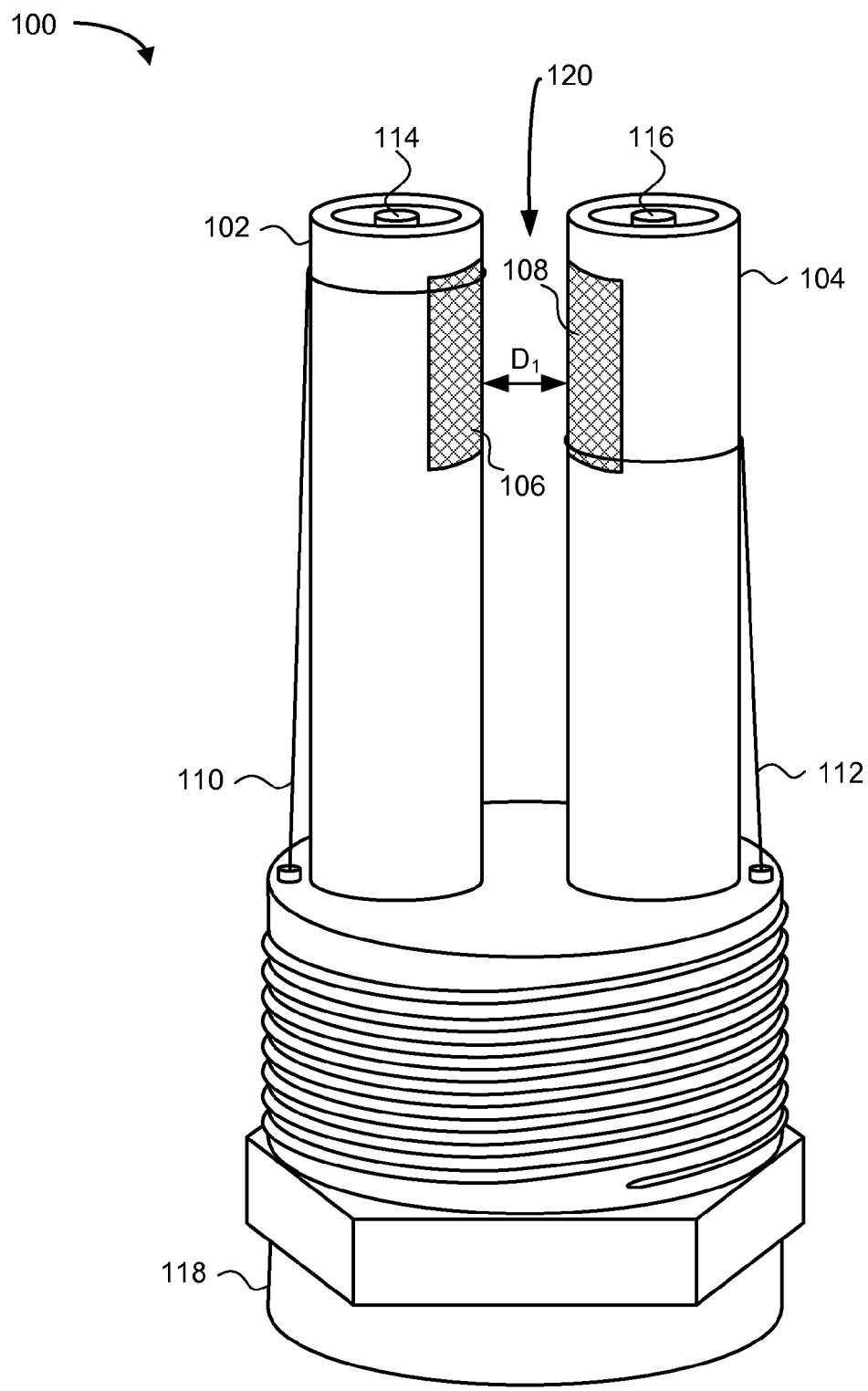
FIG. 1 depicts a schematic diagram of one embodiment of a sensor assembly.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments of a particulate matter sensor are described herein, at least some of the described embodiments detect particulate matter within an exhaust stream. The sensor includes two surface electrodes on two rigid tubes. The surface electrodes are oriented to face each other. An air gap between the two surface electrodes allows exhaust to flow between the two surface electrodes. In some embodiments, the first surface electrode is a detection electrode. The detection electrode is disposed on the first rigid tube. The second surface electrode is a bias electrode and is disposed on the second rigid tube. The bias surface electrode has an applied voltage, also referred to as a bias voltage. As the particulate matter in the exhaust stream passes between the bias and detection surface electrodes, a charge builds up or a current flows on the detection surface electrode. An electronic controller measures an electrical characteristic in the form of a charge, current, or voltage, and determines an amount of particulate matter in the exhaust.

Additionally, as exhaust passes through the sensor, particulate matter may build up on the surfaces of the sensor. Deposits on the detection and bias surface electrodes can distort particulate matter measurements. In some embodiments, each rigid tube of the sensor includes a heater post located in an internal cavity within the tube. A wire heater may be wrapped around the heater post. The wire heater is configured to generate heat sufficient to burn off the particulate matter deposits on the surfaces of the rigid tube. In particular, the heaters may burn off particulate matter deposits on the detection and bias surface electrodes.

Also, in some embodiments, by locating the surface electrodes on two separate rigid tubes, typical problems relating to electrical leakage through intermediate ceramic layers can be avoided. While conventional ceramic sensors which include electrodes separate by an intermediate ceramic layer can exhibit electrical leakage at high voltages and/or high operating temperatures (due to decreased electrical insulating properties of the intermediate ceramic layer), embodiments of the particulate matter sensor described herein do not have an intermediate ceramic layer interposed between the electrode layers and, therefore, do not exhibit electrical leakage between the surface electrodes. In other words, embodiments with the surface electrodes mounted on separate structures (e.g., rigid tubes) have reduced charge leakage which results in reduced signal distortion, compared with conventional ceramic particulate matter sensors made from a single stack of ceramic and conductive layers.

FIG. 1 depicts a schematic diagram of one embodiment of a sensor assembly 100. The illustrated sensor assembly 100 includes a first rigid tube 102, a second rigid tube 104, a detection surface electrode 106, a bias surface electrode 108, a first electrical connection 110, a second electrical connection 112, a first heater post 114, a second heater post 116, and a sensor base 118. Although the sensor assembly 100 is shown and described with certain components and functionality, other embodiments of the sensor assembly 100 may include fewer or more components to implement less or more functionality.

In some embodiments, the first rigid tube 102 is made of non-conductive ceramic. For example, the first rigid tube 102 may be made of alumina ($Al_2O_3$), magnesia (MgO), magnesium aluminate spinell ($MgAl_2O_4$), or other types of spinells. Other embodiments may use other types of ceramics and/or non-conductive materials. In one embodiment, the first rigid tube 102 has a substantially cylindrical geometry. The first rigid tube 102 has an outer diameter that is constant along the length of the first rigid tube 102. In some embodiments, the first rigid tube 102 has an inner diameter to retain the structural stability of the first rigid tube 102. In one embodiment, the outer diameter of the first rigid tube 102 is between about 6 to 7 mm (approximately 0.25 inch). In other embodiments, the outer diameter of the first rigid tube 102 is between about 5 to 10 mm. In some embodiment, the wall thickness of the first rigid tube 102 is about 1 mm (approximately 30 to 40 thousandths of an inch). In other embodiment, the wall thickness of the first rigid tube 102 is about 0.5 to 2 mm. The inner diameter of the first rigid tube 102 depends on the outer diameter and the wall thickness of the first rigid tube 102. However, at least some embodiments of the first rigid tube 102 have an inner diameter that is sufficiently large to fit the first heater post 114 within the interior cavity of the first rigid tube 102. The size of the first heater post 114 may depend on the type of heating element which is implemented by the first heater post 114. Other embodiments may use other dimensions for the inner or outer diameters, or the wall thickness, of the first rigid tube 102.

The first rigid tube 102 is aligned parallel to the second rigid tube 104. The second rigid tube 104 is substantially similar to the first rigid tube 102. In some embodiments, the first and second rigid tubes 102 and 104 are formed of the same ceramic materials. In other embodiments, the first and second rigid tubes 102 and 104 are formed of different ceramic or non-conductive materials. The first and second rigid tubes 102 and 104 define an air gap 120. The air gap 120 allows air, or exhaust, to flow between the first and second rigid tubes 102 and 104. The air gap 120 separates the first and second rigid tubes 102 and 104, as well as the corresponding detection and bias surface electrodes 106 and 108 by a distance $D_1$.

The detection surface electrode 106 is disposed on the outer surface of the first rigid tube 102. The detection surface electrode 106 is made of a conductive material. The detection surface electrode 106 may include, for example, a metallic foil made of platinum, gold, tungsten, nickel, or a mullite-based material. Other embodiments may use or include other types of conductive materials. In some embodiments, the detection surface electrode 106 is painted onto an outer surface of the first rigid tube 102. In another embodiment, the detection surface electrode 106 is printed onto the outer surface of the first rigid tube 102. In other embodiments, the detection surface electrode 106 is chemically or physically deposited onto the outer surface of the first rigid tube 102.

The bias surface electrode 108 is substantially similar in structure and material to the detection surface electrode 106. In particular, the bias surface electrode 108 is disposed on an outer surface of the second rigid tube 104. The detection and surface electrodes 106 and 108 may be between about 1.0 to 2.0 square cm. In another embodiment, the surface area of each of the surface electrodes 106 and 108 is between about 0.5 to 4.0 square cm. Other embodiment may have surface electrodes 106 and 108 with smaller or larger surface areas.

In some embodiments, the bias surface electrode 108 is biased and generates an electric field. In one embodiment, a bias voltage is applied to the bias surface electrode 108. The bias voltage of the bias surface electrode 108 may be, for example, between about 1 to 10,000 Volts. Alternatively, the bias voltage may be between about 500 to 5,000 Volts. Other embodiments may use other bias voltages. By biasing the bias surface electrode 108, the particulate matter passing in the exhaust stream between the bias surface electrode 108 and the detection surface electrode 106 affects a charge or current on the detection surface electrode 106. The charge or current (or voltage) on the detection surface electrode 106 can be correlated with a particulate matter concentration within the exhaust stream. In this way, the detection surface electrode 106 facilitates detection of the particulate matter in the exhaust stream.

The detection and bias surface electrodes 106 and 108 are connected to the first and second electrical connections 110 and 112, respectively. In one embodiment, the first electrical connection 110 is used to measure the charge, current, or voltage on the detection surface electrode 106. The second electrical connection 112 is used to supply the bias voltage to the bias surface electrode 108. FIG. 1 shows the first and second electrical connections 110 and 112 looped around the outside of the rigid tubes 102 and 104 and the surface electrodes 106 and 108 to mechanically connect to the surface electrodes 106 and 108. In another embodiment, the electrical connections 110 and 112 may be connected to the surface electrodes 106 and 108 by a thermal process such as brazing. The electrical connections 110 and 112 extend down to the sensor base 118. Other embodiments may implement other connection configurations for the first and second electrical connections 110 and 112.

In order to measure the charge on the detection surface electrode 106, some embodiments of the sensor 100 include a charge amplifier (not shown) coupled to the detection surface electrode 106 via the first electrical connection 110. The charge amplifier may be calibrated to measure an accumulated electric charge on the detection surface electrode 106 as particulate matter flows within the exhaust stream between the detection and bias surface electrodes 106 and 108. The electric charge that accumulates on the detection surface electrode 106 varies with the mass concentration of particulate matter in the exhaust conduit. Thus, the charge amplifier may generate an output voltage corresponding to the measured accumulated electric charge. In general, the charge amplifier obtains a voltage proportional to the charge and yields a low output impedance. Hence, the charge amplifier also may be referred to as a charge-to-voltage converter.

Alternatively, in some embodiments, current flow on the detection surface electrode 106 and through the first electrical connection 110 may be measured in order to determine an amount of particulate matter in the exhaust stream. In another embodiment, voltage or another electrical parameter may be measured to determine the amount of particulate matter in the exhaust stream.

In one embodiment, although not depicted in detail in FIG. 1, the detection and bias surface electrodes 106 and 108 are offset relative to each other to reduce the chance of an electrical short occurring between the electrical components of the first rigid tube 102 and the electrical components of the second rigid tube 104. In particular, the detection and bias surface electrodes 106 and 108 are offset relative to each other, along a longitudinal axis of the first and second rigid tubes 102 and 104, to reduce the chance of an electrical short occurring between the bias surface electrode 108 and the first electrical connection 110 or between the detection surface electrode 106 and the second electrical connection 112. However, it should be noted that offsetting the surface electrodes 106 and 108 may reduce the amount of overlap between the surface electrodes 106 and 108 and, hence, reduce the effective size of the surface electrodes 106 and 108 (or, alternatively, increase the effective distance, $D_1$, between the surface electrodes 106 and 108).

The first and second heater posts 114 and 116 are located within the internal cavities first and second rigid tubes 102 and 104. The heater posts 114 and 116 are described in more detail below with reference to FIG. 2. The sensor base 118 allows the sensor 100 to be mounted into an exhaust channel wall (e.g., an exhaust pipe).

Figure 2:
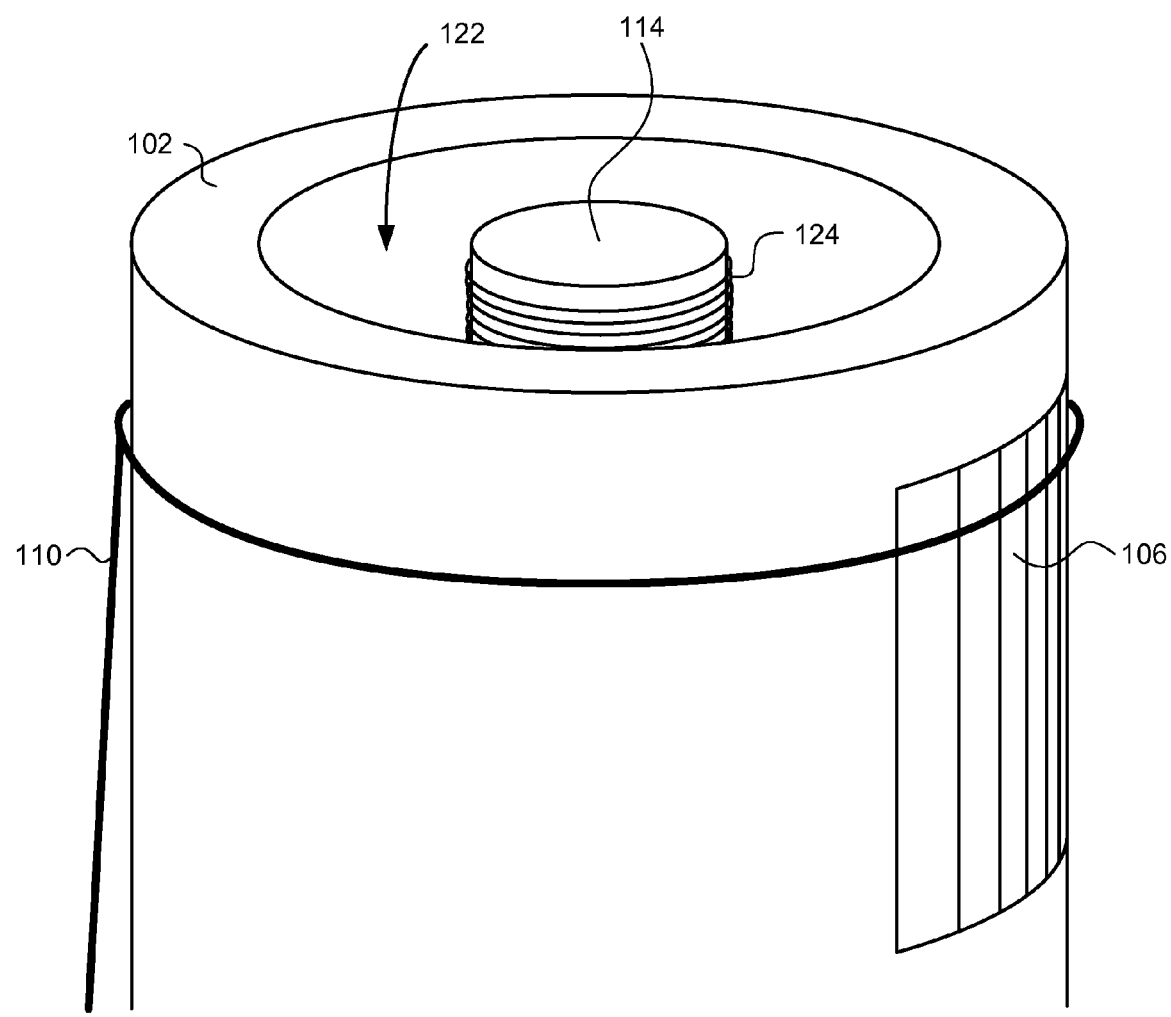
FIG. 2 depicts a schematic diagram of one embodiment of the heater post within the first rigid tube of the sensor assembly of FIG. 1.

FIG. 2 depicts a schematic diagram of one embodiment of the heater post 114 within the first rigid tube 102 of the sensor assembly 100 of FIG. 1. In one embodiment, the heater post 116 and the second rigid tube 104 are similar in structure and function to the heater post 114 and the first rigid tube 102, respectively.

The shape of the first rigid tube 102 forms an internal cavity 122. In one embodiment, the heater post 114 is centrally mounted within the internal cavity 122. Alternatively, the heater post 114 may be offset, for example, to be near the detection surface electrode 106. A heater element 124 is disposed on the outer surface of the first heater post 114. In one embodiment, the heater element 124 is separated by a distance from the first rigid tube 102. More specifically, there may be an air gap between the heater element 124 and the ceramic structure of the first rigid tube 102. By having the air gap between the heater element 124 and the first rigid tube 102, the temperature of the first rigid tube 102 can be maintained lower so that the first rigid tube 102 does not get too hot and become electrically conductive. If the first rigid tube 102 were to become electrically conductive, then a disruptive current can flow from the heater element 124 to the surface electrode 106 if the heater element 124 were to contact the inner surface of the first rigid tube 102.

In one embodiment, the heater element 124 is a resistive heater element. For example, the heater element 124 may be a resistive wire wrapped around the heater post 114. In one embodiment, the heater element 124 is configured to generate heat substantially continuously. In some embodiments, the heater element 124 is configured to generate heat intermittently. Some embodiments may incorporate a timing scheme to control the heater element 124, as described in more detail below with reference to FIG. 3.

In one embodiment, the heater element 124 maintains specific operating temperatures for the corresponding rigid tube 102 and, in particular, the corresponding detection surface electrode 106. The heater 124 may operate continuously, periodically, or on some other non-continuous basis. In one embodiment, the heater element 124 operates within a temperature range of approximately 200° C. or higher to burn off particulate matter from the rigid tube 102, which may include burning off particulate matter accumulated on the detection surface electrode 106. In some embodiments, the heater element 124 operates within a temperature range of approximately 400° C. or higher. Other embodiments of the heater element 124 may operate at other temperatures.

Figure 3:
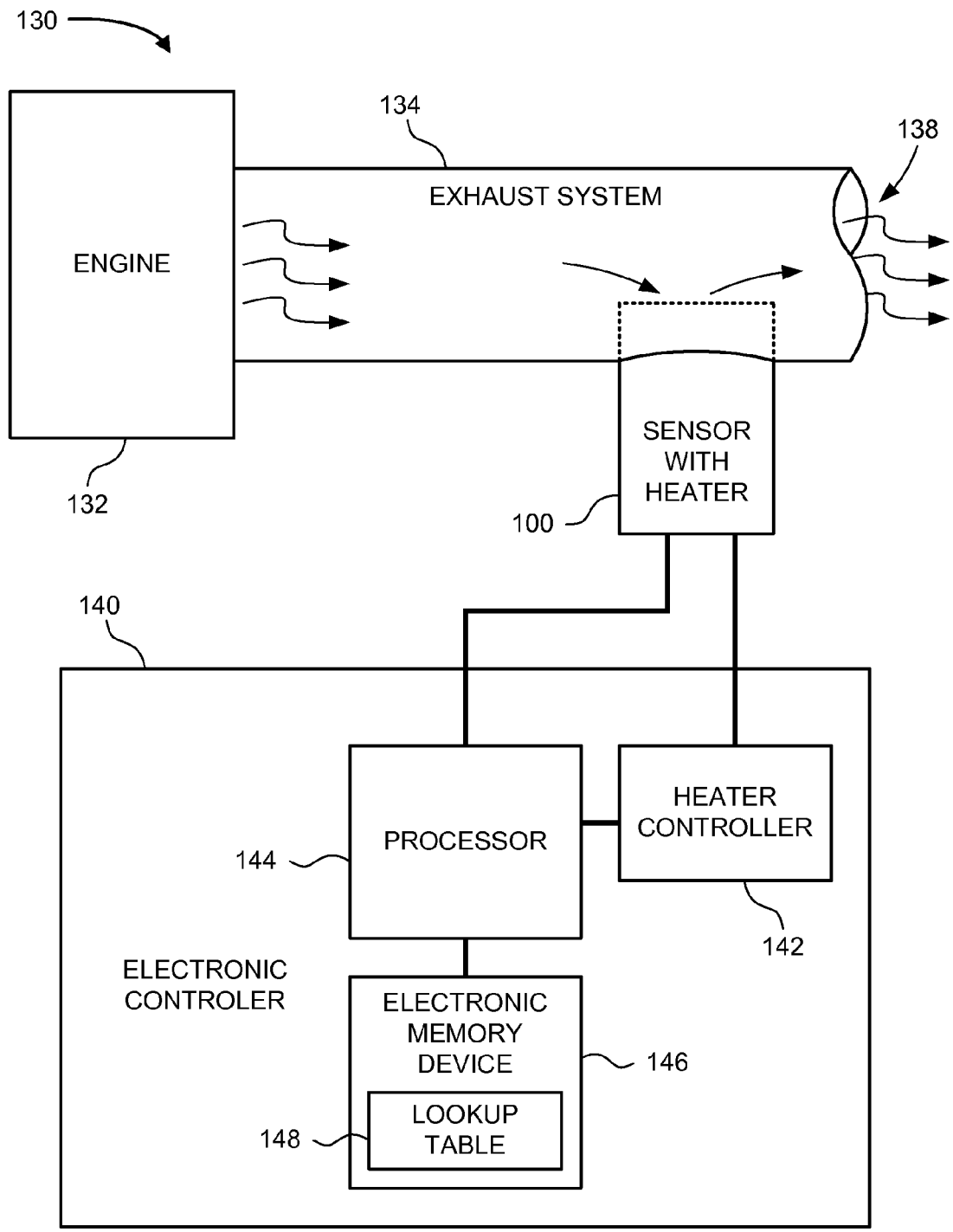
FIG. 3 depicts a schematic block diagram of one embodiment of a particulate matter detection system.

FIG. 3 depicts a schematic block diagram of one embodiment of a particulate matter detection system 130. The illustrated embodiment includes the particulate matter sensor 100, an engine 132, and an exhaust system 134. The engine 132 produces exhaust which moves through the exhaust system 134. The exhaust system 134 facilitates flow of the exhaust gases to an exhaust outlet 138. The sensor 100 is at least partially inserted into the exhaust system 134 to detect particulate matter in the exhaust stream. As the exhaust in the exhaust system 134 passes over and through the sensor 100, the sensor 100 detects the particulate matter within the exhaust by measuring changes in the electrical characteristics at the sensor 100, as described above.

The particulate matter detection system 130 also includes an electronic controller 140. The electronic controller 140 includes a heater controller 142, a processor 144, and an electronic memory device 146. The sensor 100 relays the sensor signal to the processor 144 of the electronic controller 140. In some embodiments, the processor 144 analyzes the sensor signal from the sensor 100. If the sensor signal is corrupted, the processor 144 sends a control signal to the heater controller 142. The heater controller 142 activates one or more heaters on the sensor 100 to burn off particulate matter deposits that might corrupt the sensor signal from the sensor 100. In some embodiments, the processor 144 sends the control signal to the heater controller 142 to activate the heater on the sensor 100 according to a timing scheme or on some other substantially continuous or non-continuous basis.

If the sensor signal from the sensor 100 is not corrupt, the processor 144 compares the sensor signal with data stored in a lookup table 148 on the electronic memory device 146 to determine one or more qualities of the exhaust in the exhaust system 134. For example, the processor 144 may determine an amount of particulate matter in the exhaust stream. The processor 144 also may compare the sensor signal from the sensor 100 with data from the lookup table 148 to estimate, for example, a mass concentration of particulate matter in the exhaust stream. In other embodiments, the electronic controller 140 facilitates detection of one or more other qualities of the exhaust in the exhaust system 134.

Some embodiments of the particulate measurement system 130 also may include one or more emissions control elements (not shown) to emit neutralizing chemicals into the exhaust system 134 either before or after the sensor 100. It should also be noted that embodiments of the sensor 100 may be tolerant of fluctuations of certain gaseous constituents in an exhaust gas environment. In this way, the sensor 100 may be calibrated to measure particular chemicals or materials within an exhaust stream.

It should also be noted that the sensor 100 may be used, in some embodiments, to determine a failure in another component of the particulate matter detection system 130. For example, the sensor element 100 may be used to determine a failure of a particulate matter filter (not shown) within the exhaust system 134. In one embodiment, a failure within the particulate matter detection system 130 may be detected by an elevated signal generated by the sensor 100. In some embodiments, the particulate matter detection system 130 includes an alarm to indicate a detected failure of the sensor 100 or other component of the particulate matter detection system 130. In some embodiments, the sensor 100 also could be coupled to another sensor or detector such as a mass flow meter.

Figure 4:
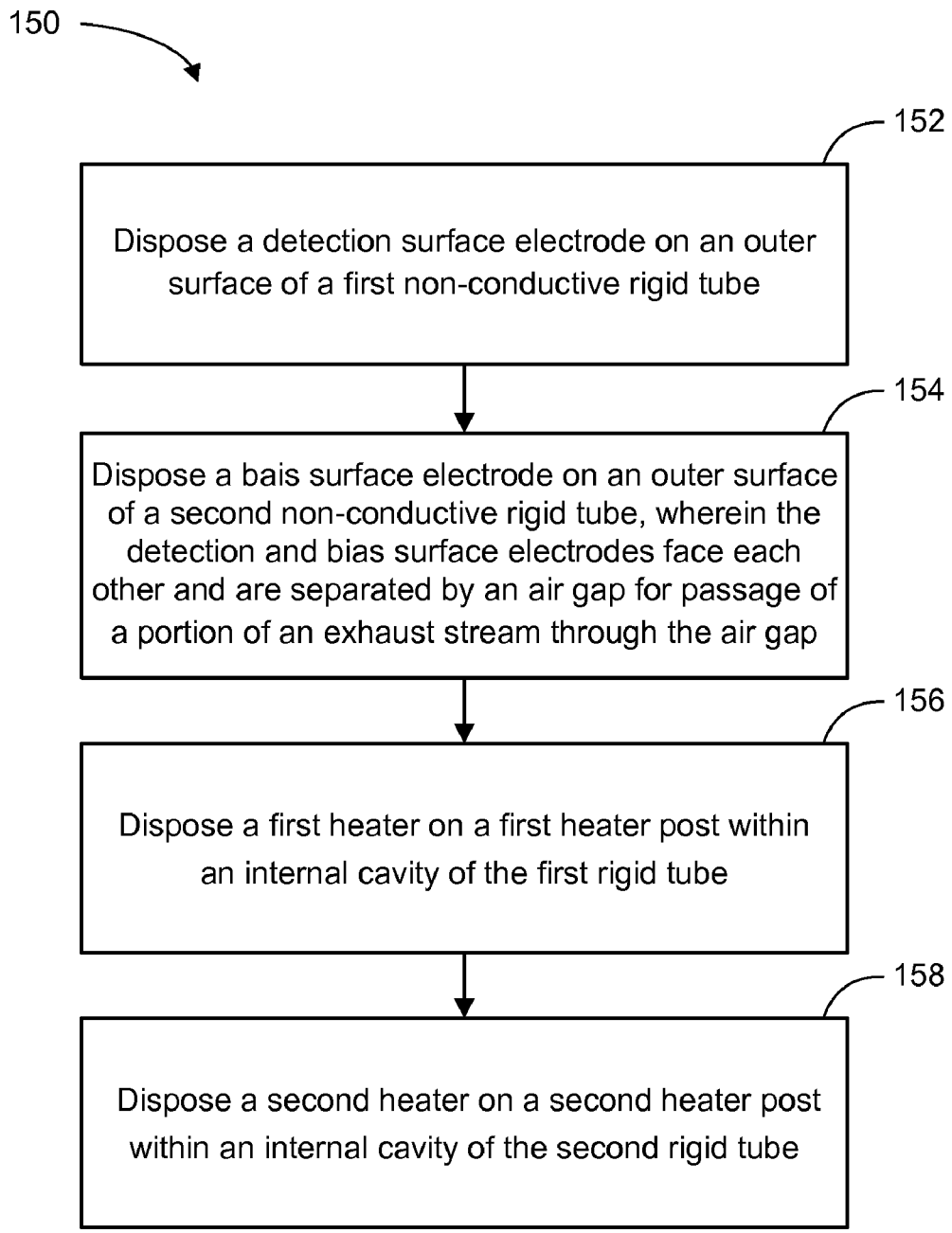
FIG. 4 depicts a flow chart diagram of one embodiment of a method for making a particulate matter concentration sensor.

FIG. 4 depicts a flow chart diagram of one embodiment of a method 150 for making a particulate matter sensor such as the sensor 100 of FIG. 1. Although the method 150 is described in conjunction with the sensor 100 of FIG. 1, other embodiments of the method 150 may be implemented with other particulate matter sensors.

The illustrated method 150 includes disposing 152 a detection surface electrode 106 on an outer surface of a first non-conductive rigid tube 102. The method 150 also includes disposing 154 a bias surface electrode 108 on an outer surface of a second non-conductive rigid tube 104. The detection and bias surface electrodes 106 and 108 face each other and are separated by an air gap 120 with a distance $D_1$. The air gap 120 allows a portion of an exhaust stream to pass between the detections and bias surface electrodes 106 and 108. The method 150 also includes disposing 156 a first heater 124 on a first heater post 114 within an internal cavity 122 of the first rigid tube 102. The method 150 also includes disposing 158 a second heater on a second heater post 116 within an internal cavity of the second rigid tube 104. The heaters may be operated according to the electronic controller 140 of FIG. 3 to burn off particulate matter on the rigid tubes 102 and 104 and/or the detection and bias surface electrodes 106 and 108. The depicted method 150 then ends.

Figure 5:
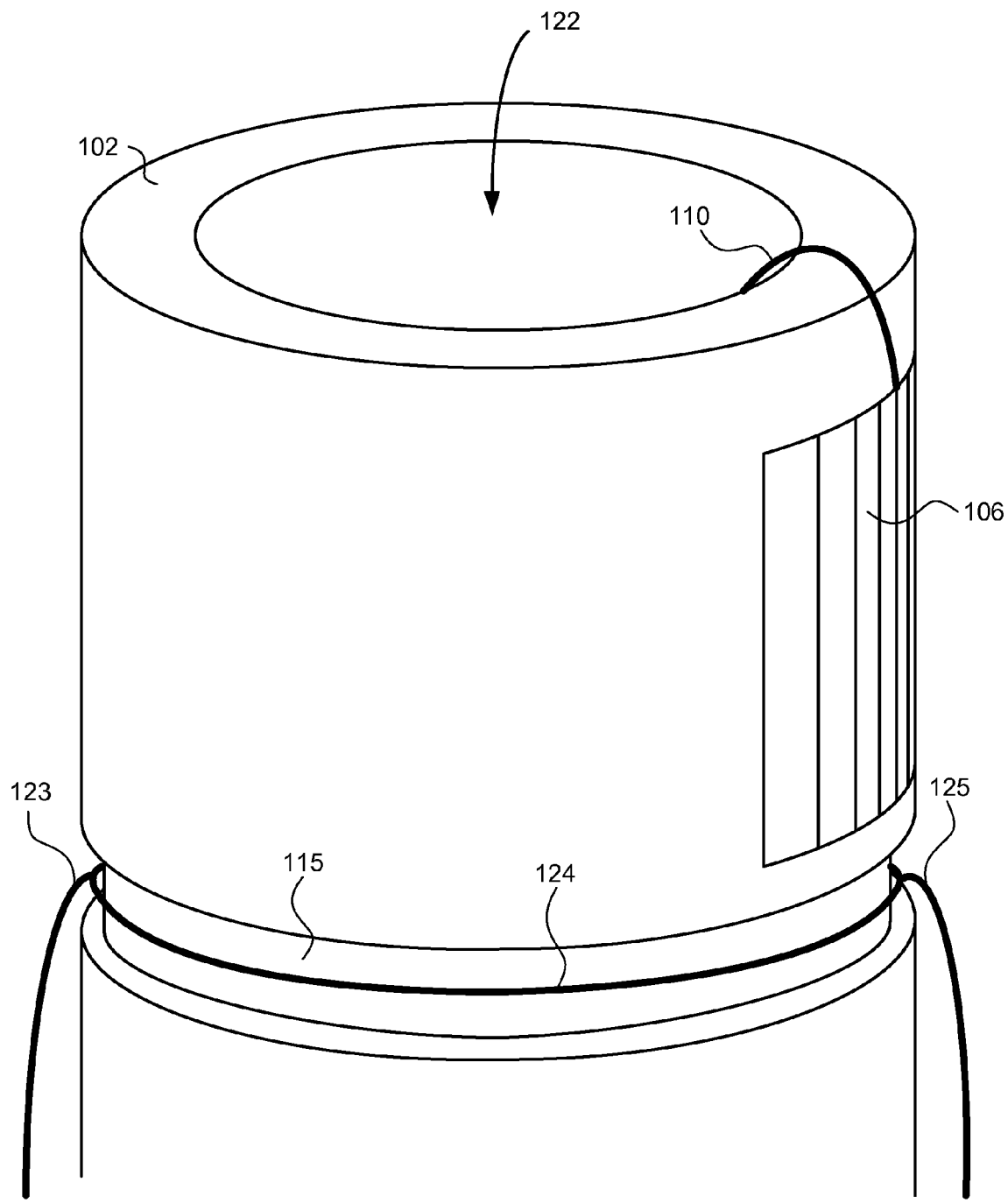
FIG. 5 depicts a schematic diagram of another embodiment with the heater element mounted to the outside of the first rigid tube of the sensor assembly of FIG. 1.

FIG. 5 depicts a schematic diagram of another embodiment with the heater element 124 mounted to the outside of the first rigid tube 102 of the sensor assembly 100 of FIG. 1. In some embodiments, the rigid tube 102 includes a surface groove 115, which at least partially contains the heater element 124. The heater element 124 may be located on the exterior of the first rigid tube 102 (e.g., within the groove 115) to substantially reduce carbon tracks around the heater element 124. In some embodiments, the heater element 124 is a closed loop with a source (i.e., supply) connection 123 and a ground connection 125. The source and ground connections 123 and 125 may be attached to opposite sides of the heater element 124 (e.g., approximately 180 degrees around the first rigid tube 102) so that current flows through both sides of the wire heater element 102. By placing the heater 124 on the outside of the first rigid tube 102, as explained herein, some embodiments prevent formation of a carbon track between the coils of a helical wound wire. In the depicted embodiment, the first electrical connection 110 is connected to the surface electrode 106 by a wire which runs through the internal cavity 122 of the first rigid tube 102. Other embodiments may use other types of connections for the heater element 124 and/or the surface electrode 106.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A sensor comprising:
   a first rigid tube;
   a second rigid tube mounted substantially parallel to the first rigid tube;
   a detection surface electrode disposed on an outer surface of the first rigid tube, wherein the detection surface electrode is disposed to face the second rigid tube; and
   a bias surface electrode disposed on an outer surface of the second rigid tube, wherein the bias surface electrode is disposed to face the detection surface electrode on the first rigid tube with a gap between the detection surface electrode and the bias surface electrode.

2. The sensor of claim 1, wherein the detection and bias surface electrodes each comprise a conductive foil disposed on the outer surfaces of the first and second rigid tubes.

3. The sensor of claim 1, wherein the detection and bias surface electrodes each comprise a conductive material printed on the outer surfaces of the first and second rigid tubes.

4. The sensor of claim 1, wherein the detection surface electrode is offset, along a longitudinal axis of the first rigid tube, relative to the bias surface electrode.

5. The sensor of claim 1, wherein the detection surface electrode is electrically connected to an electrical connection within a central cavity of the first rigid tube.

6. The sensor of claim 1, wherein the bias surface electrode is electrically connected to an electrical connection within a central cavity of the second rigid tube.

7. The sensor of claim 1, wherein a bias voltage is applied to the bias surface electrode.

8. The sensor of claim 7, wherein the bias voltage comprises a voltage within a range of approximately 1 to 10,000 Volts.

9. The sensor of claim 8, wherein the bias voltage comprises a voltage within a range of approximately 500 to 5,000 Volts.

10. The sensor of claim 1, wherein the first and second rigid tubes each comprise a ceramic material.

11. The sensor of claim 1, further comprising a heater mounted within a surface groove of at least one rigid tube of the first and second rigid tubes, wherein the heater is configured to apply heat to approximately a surface electrode location on the at least one rigid tube.

12. The sensor of claim 11, further comprising:
    a source electrical connection coupled to a first side of the heater, the source electrical connection to provide a source voltage to the heater; and
    a ground electrical connection coupled to a second side of the heater approximately on an opposite side of the heater, wherein the source electrical connection and the ground electrical connection facilitate current flow through the entire heater during operation of the heater.

13. The sensor of claim 1, further comprising a heater mounted within at least one rigid tube of the first and second rigid tubes, wherein the heater is configured to apply heat to approximately a surface electrode location on the at least one rigid tube.

14. The sensor of claim 13, wherein the heater comprises a resistance heater comprising a metal wire wound around the heater post.

15. The sensor of claim 13, wherein the heater is configured to generate heat substantially continuously.

16. The sensor of claim 13, wherein the heater is configured to generate heat intermittently.

17. The sensor of claim 13, wherein the heater is located at a distance from an interior surface of the at least one rigid tube of the first and second rigid tubes to define an air gap between the heater and the interior surface of the at least one rigid tube.

18. The sensor of claim 1, further comprising:
    a first heater disposed on a first heater post within an internal cavity of the first rigid tube, the first heater to apply heat to the detection surface electrode; and
    a second heater disposed on a second heater post within an internal cavity of the second rigid tube, the second heater to apply heat to the bias surface electrode.

19. A system for detecting particulate matter, the system comprising:
    a sensor to detect the particulate matter within an exhaust stream, the sensor comprising:
      a pair of non-conductive rigid tubes;
      a detection surface electrode disposed on one of the rigid tubes,
      wherein the detection surface electrode faces the other non-conductive rigid tube; and
      a bias surface electrode disposed on the other rigid tube, wherein the bias surface electrode faces the detection surface electrode and is separated from the detection surface electrode by an air gap for passage of a portion of the exhaust stream through the air gap; and
    an electronic controller to determine an amount of the particulate matter within the exhaust stream.

20. The system of claim 19, wherein the detection and bias surface electrodes are disposed on outer surfaces of the rigid tubes.

21. The system of claim 19, further comprising a plurality of heaters, wherein at least one heater is disposed within each rigid tube, wherein the heaters are configured to apply heat to the detection and bias surface electrodes on the rigid tubes.

22. The system of claim 21, wherein the electronic controller is further configured to control a frequency of operation of the heaters.

23. The system of claim 21, wherein the electronic controller is further configured to control a temperature of operation of the heaters.

24. The system of claim 19, further comprising a heater to burn off particulate matter from the detection and bias surface electrodes.

25. The system of claim 19, further comprising a sensor base to at least partially enclose an end of the sensor, the sensor base to allow the portion of the exhaust stream to pass between the detection and bias surface electrodes.

26. The system of claim 19, further comprising an electrical connection to each of the detection and bias surface electrodes, wherein each electrical connection comprises a metallic wire along an outside surface of the corresponding non-conductive rigid tubes.

27. A method of operation of the system of claim 19, the method comprising detecting a failure of a particulate matter filter within the exhaust stream based on the amount of the particulate matter within the exhaust stream.

28. A method of operation of the system of claim 19, the method comprising controlling a combustion parameter of an engine from which the exhaust stream originates based on the amount of the particulate matter within the exhaust stream.

29. A method of operation of the system of claim 19, the method comprising controlling the amount of particulate matter within the exhaust stream from an engine based on the amount of the particulate matter within the exhaust stream.

30. A method for making a particulate matter sensor, the method comprising:
- disposing a detection surface electrode on an outer surface of a first non-conductive rigid tube;
- disposing a bias surface electrode on an outer surface of a second non-conductive rigid tube, wherein the detection and bias surface electrodes face each other and are separated by an air gap for passage of a portion of an exhaust stream through the air gap;
- disposing a first heater on a first heater post within an internal cavity of the first rigid tube, the first heater to apply heat to burn off particulate matter from the first non-conductive rigid tube; and
- disposing a second heater on a second heater post within an internal cavity of the second rigid tube, the second heater to apply heat to burn off particulate matter from the second non-conductive rigid tube.

31. The method of claim 30, wherein disposing the detection and bias surface electrodes further comprises painting each surface electrode onto the outer surface of the corresponding non-conductive rigid tube.

32. The method of claim 30, wherein disposing the detection and bias surface electrodes further comprises printing each surface electrode onto the outer surface of the corresponding non-conductive rigid tube.

33. The method of claim 30, wherein disposing the detection and bias surface electrodes further comprises chemically depositing each surface electrode onto the outer surface of the corresponding non-conductive rigid tube.

* * * * *